Figure 3A:
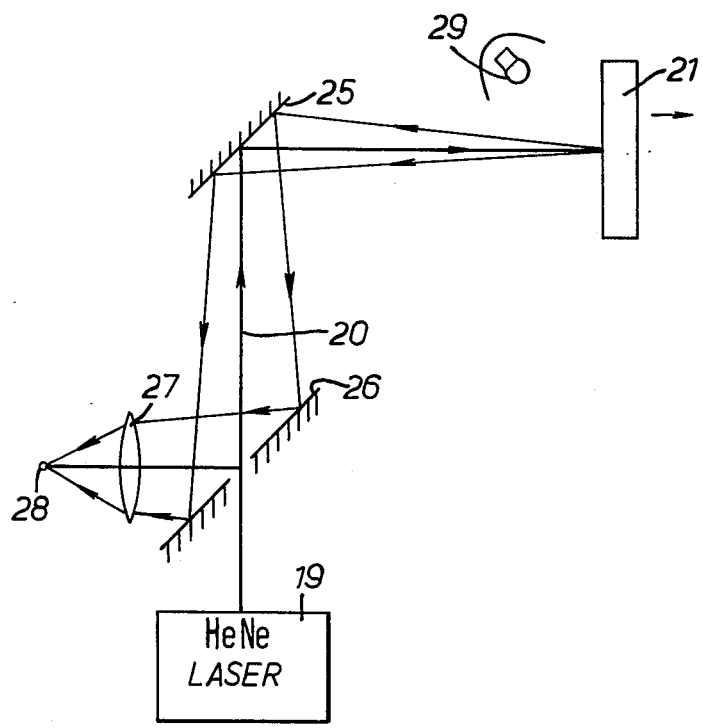

United States Patent [19]
Matthews et al.

[11] 3,976,384
[45] Aug. 24, 1976

[54] METHOD AND APPARATUS FOR DETECTING TIMBER DEFECTS

[75] Inventors: Peter Charles Matthews, Poole; Brian Herbert Beech, Broadstone, both of England

[73] Assignee: Plessey Handel und Investments A.G., Zug, Switzerland

[22] Filed: Jan. 16, 1975

[21] Appl. No.: 541,573

[30] Foreign Application Priority Data
Jan. 18, 1974 United Kingdom................ 2472/74

[52] U.S. Cl.................................. 356/200; 83/365; 250/563; 250/572; 356/237; 356/239
[51] Int. Cl.²........................................ G01N 21/16
[58] Field of Search ........... 356/199, 200, 237, 239; 250/562, 563, 572; 83/365

[56] References Cited
UNITED STATES PATENTS

| | | | |
|---|---|---|---|
| 3,165,961 | 1/1965 | Hammond | 250/572 |
| 3,694,658 | 9/1972 | Watson et al. | 356/199 |
| 3,760,667 | 9/1973 | Maxey et al. | 83/365 |

*Primary Examiner*—Vincent P. McGraw
*Attorney, Agent, or Firm*—Fleit & Jacobson

[57] ABSTRACT

Apparatus for detecting knots and the like in swan or planed timber comprising means for injecting light into the surface of the timber and means for detecting light emerging from the timber at a location spaced apart from the point or region of injection, a defect such as a knot in the timber, being indicated in dependence upon the amplitude or presence of the light emerging from the timber.

10 Claims, 8 Drawing Figures

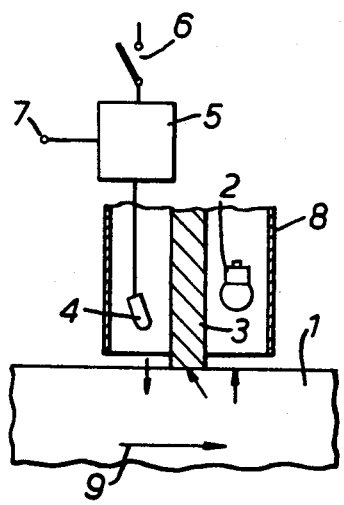
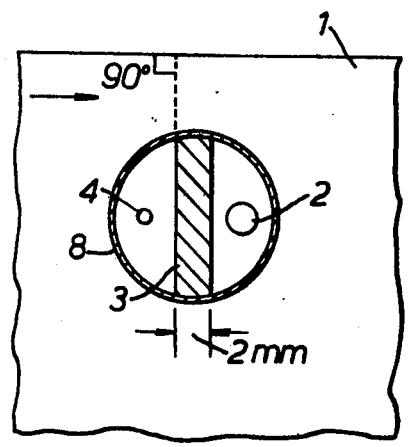
FIG. 1a.     FIG. 1b.
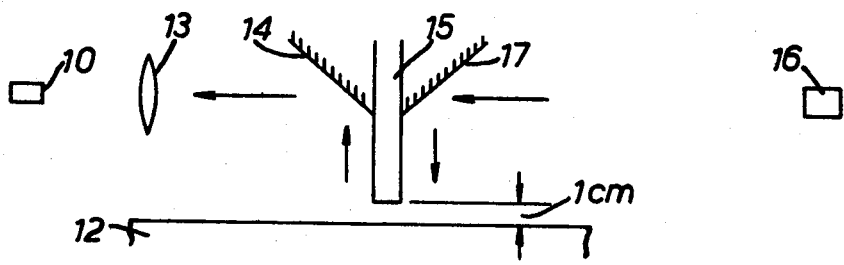
FIG. 2a.
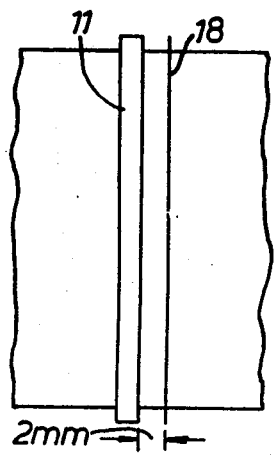
FIG. 2b.

METHOD AND APPARATUS FOR DETECTING TIMBER DEFECTS

This invention relates to optical detection apparatus and methods and it relates especially to methods and apparatus suitable for detecting defects in sawn or planed timber. The invention is concerned particularly with the detection of defects such as knots, blue stain and certain types of rot to facilitate the automatic grading of timber.

The detection of these physical defects from a direct visual image of the timber surface presents an extremely complex pattern recognition problem. This is because knots (which may take many geometric forms e.g. face knots, round knots, oval knots, splay knots, pin knots etc.) have colour and tonal qualities which embrace a very wide dynamic range. Contrast between knotwood and its surroundings is generally extremely low and even negative at times. For example springwood (usually but erroneously known as grain lines) can be photometrically indistinguishable from knotwood in the same piece. In addition since knots are sections of tree branches they themselves contain springwood which gives rise to gross tonal variations within the same knot.

Because of the above effects simple point-by-point optical analysis cannot separate knot wood from normal wood and knotwood detection utilising known pattern recognition techniques alone requires extensive spatial/tonal analysis of the surrounding area. This is to say, a point can be deemed to be knotwood only by considering a very large area surrounding the point to attempt to identify spatial/tonal qualities commonly associated with knots, the range of knot archetypes being extremely numerous and ill defined. A further difficulty is that a knot boundary, that is the point at which normal wood becomes knotwood, is not clear even to a human observer. Further complications are introduced by the nature of the timber surface e.g. sawn wood, planed wood, clean wood, discoloured wood etc.) and many of the foregoing factors apply to complicate the detection of the other timber defects just before mentioned.

According to the present invention a method suitable for detecting defects in sawn or planed timber comprises radiating light into a surface of the timber and scrutinizing with light detector means, light emerging from the timber at a location spaced apart from the region of entry, a defect in the timber between the region of entry and the said location being indicated in dependence upon the light emerging.

Thus a timber defect which is in the light transmission path will cause an attenuation of the light emerging which is detected to indicate the presence of the timber defect. Light radiated into timber travels along the grain through defect free timber and emerges at an intensity which reduces with distance from the region of entry. However light travelling along the grain is attenuated much less than light travelling across the grain. It is therefore desirable to detect light emerging from the timber at a location which is spaced apart from the region of entry substantially along the longitudinal axis of the grain. By this expedient detection of timber defects is made easier since with this arrangement in which light is transmitted along the grain, there is greater contrast between light which has travelled through defect free timber and light which has been attenuated by a timber defect.

Apparatus for carrying out the method according to the present invention may comprise means for radiating light into timber to be inspected at a region of entry, light detector means for detecting light emerging from the timber at a location spaced apart from the region of entry and for providing a first electrical signal in dependence upon such detection, means for providing a second electrical signal or reference signal and comparator means for comparing the first electrical signal with the second electrical signal and providing in dependence upon the result of such comparison an output signal related to the character of the timber under inspection.

The apparatus for carrying out the method according to the invention may comprise an opaque barrier or screen having light transmitting means on one side thereof and light detection means for providing the first electrical signal on the other side thereof and said detection means having operatively associated with it a threshold detector, whereby an output signal from the threshold detector is provided when the signal from the light detection means bears a predetermined relationship to a present threshold level signal constituting the said second electrical signal.

The apparatus may be spaced manually or automatically a predetermined distance from the timber to be inspected. A typical spacing distance may be about 1 cm. or less whilst a typical barrier thickness or spacing between the light transmission means and light detection means may be of the order of 2 mm.

Means may be provided for scanning an image of the surface of timber to be inspected across the detector means as the timber is moved past a station whereat the apparatus is located.

The detector means may comprise a plurality of photodiodes or other photo sensitive devices arranged side-by-side to form an array and extend across an inspection gate through which timber to be examined is passed.

Alternatively the second electrical signal may be provided by a further light detector means responsive to light transmitted through the timber from the region of entry in a direction substantially orthogonally to the direction of light transmitted from the region of entry to the said location and emerging at a further defined region.

Thus light is transmitted from the region of entry along the grain of the timber to the said location, and across the grain to the said further defined region or vice versa. Thus since in good wood light travels more readily along the grain than across the grain a comparison between the light intensity at the said location and the further defined region which are orthogonally disposed with respect to the region of entry will give an indication of the character of the wood therebetween.

An alternative preferred form of the apparatus may comprise means for directing a spot of light on to the surface of the timber to be inspected the spot constituting the region of entry, means for focussing light reflected from the location spaced apart from the spot on the the light detector means and means for scanning the surface of the timber with the spot and for contemporaneously scanning the light detector means with light reflected from the said location.

The alternative form of the apparatus may include further light detector means the means for focussing light reflected from the said location being used also to focus light reflected from a further defined region disposed and spaced substantially orthogonally from said location with respect to the said spot, said further detector means providing the said second electrical signal.

Another light detector may also be provided on to which light reflected from the spot or region of entry may be focussed by the means for focussing light reflected from the said location.

The means for producing the light spot may comprise a laser, and light received by the various detectors may be passed through a filter at the laser wavelength. For example a helium neon laser may be used with a corresponding filter. Thus background light will be largerly ignored by the various light detectors.

The means for focussing light reflected from the region spaced from the spot may comprise a lens system.

The scanning means may comprise a scanner mirror system.

The alternative form of apparatus may comprise a further mirror through a hole in which light is directed on to the timber from the laser via the scanner mirror system, the further mirror being used to reflect light received from the timber via the scanner mirror system through the lens system and on to the light detector means and/or further light detector means and the said other light detector.

Although almost any type of timber defect will be detected by a system utilising differential detection as just before described different types of defects cannot be discriminated between without further apparatus. In order to discriminate between various defects the colour of the wood may be examined. The apparatus may therefore additionally include two additional light detectors responsive to specified colours of the regions of the timber under inspection. One of the additional detectors may have associated with it a red filter and be responsive to deep red light and the other additional detector may have associated with it a blue filter and therefore be responsive to blue light. The relative levels of the signals from the additional detectors may be compared and the result of the comparison used to categorise a defect. A defect which reflects more blue than red light is likely to be rot whereas a defect which is generally red is most likely to be a knot.

Signals from the light detector means may be fed to character recognition apparatus whereby various defects are discriminated between on the basis of their shape. The apparatus may comprise storage means in which signals relating to a predetermined area of timber are stored and interrogated or sampled for the purpose of recognising predetermined features appertaining to various defects. The features detected may be compared with features stored and characteristic of predetermined defects the occurrence of a predetermined defect being indicated in dependence upon the result of such comparison.

The apparatus may include means for analysing defects indicated as being associated with a particular piece of timber and for grading it accordingly.

Although the methods and apparatus of the present invention utilise visible light, it is envisaged that light in the non-visible spectrum may be used especially infra red light, and although the method and apparatus of the invention is eminently suitable for detecting defects in sawn timber they may be used for detecting flaws and the like in other materials which are translucent.

Figure 3B:
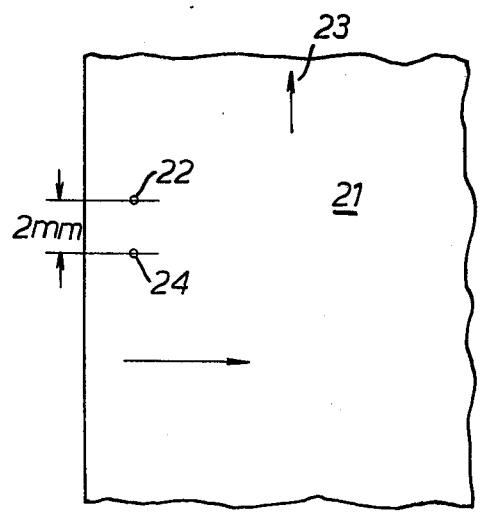
Figure 4:
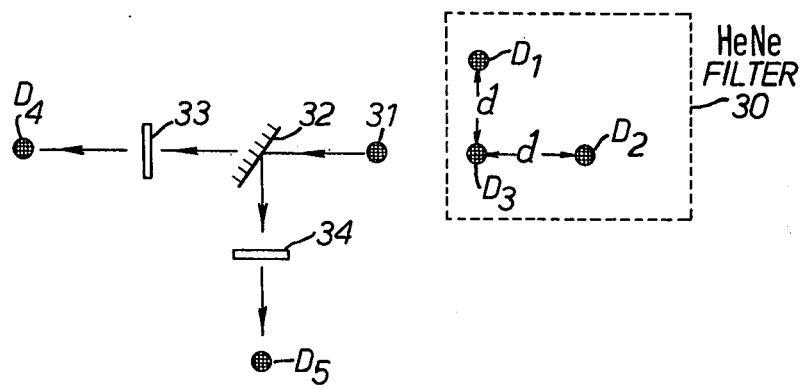
Figure 5:
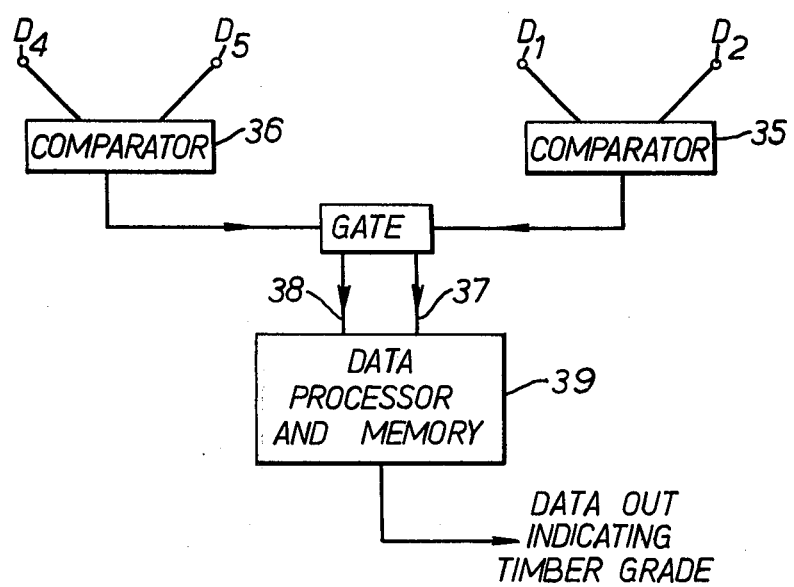

Some exemplary embodiments of the invention will now be described with reference to the accompanying drawings in which:

FIG. 1a is a generally schematic side view partly in section of apparatus for detecting defects in timber, FIG. 1b is a generally schematic plan view of the apparatus shown in FIG. 1a, FIG. 2a is a generally schematic side view of apparatus for optically scanning timber to detect certain defects and FIG. 2b is a plan view of part of the apparatus shown in FIG. 2a, FIG. 3a is a generally schematic side view of alternative apparatus for optically scanning timber for the purpose of detecting certain defects, FIG. 3b is a generally schematic plan view showing part of the apparatus of FIG. 3a, FIG. 4 is a generally schematic block diagram of a detector system, and FIG. 5 is a block schematic diagram of a timber grading machine utilising output signals from the detector of FIG. 4.

Before describing the invention with reference to the accompanying drawings the problems and technology associated with the detection of defects in timber will be discussed. The majority of cells in softwood timber are tracheids, and a tracheid cell is an elongate cell typically 3 to 5 mm. long having a very large aspect of ratio which is in the order of 50 : 1. For the purpose of the present invention the tracheid cell may be considered to be a closed cylinder. The cell wall thickness varies considerably being very thin in springwood which is produced by fast growth at the beginning of the growing season and considerably thicker in summerwood. In sapwood the cell contents are a starchy sugary compound which becomes more solid in hardwood where it is known as lignin and contains no free sugar compounds. The tracheid cells give rise to the grain stucture of timber the grain direction being the longitudinal axis of the tracheids.

When light is incident on the surface of time the majority of the light is scattered and reflected away from the surface the remainder entering the tracheid cells where it is scattered by the cell contents. Clearly light scattered along the axis of the cells encounter fewer cell walls per unit length than light travelling across the cells. If the intensity of light scattered out of the surface of the wood surrounding a point of incident illumination is plotted then lines of uniform light intensity are obtained which show the internal propagation to be highly directional and peaking to a maximum along the grain or cell axis direction and being minimum at a direction perpendicular to the longitudinal axis of the grain. The contrast between along the grain signals and across the grain signals is greatest (in the region of 50 : 1) at a distance of 2 mm. from the source of illumination and it is this effect which is utilised to identify knotwood and certain other timber defects. There is an abrupt and and large tracheid alignment change associated with all knots which is quite independent of colour. That is, a knot is really a section of branch growing at or near an angle perpendicular to the tree and there is always a large change of tracheid direction for any section of the branch, and this can be detected by a method according to the present invention involving injecting light into the timber cells.

Apparatus for carrying out the method according to the invention and for detecting defects in a piece of timber 1 comprises a light source which in the present example is a filament lamp 2 arranged on one side of a barrier 3 which forms a foot at one end which makes contact with the timber 1. On the side of the barrier 3 there is located a light detector 4 feeding a threshold detector or comparator 5 providing an output signal on line 7 when the light incident on the detector 4 produces an electrical signal which exceeds a threshold level applied to input terminal 6. The apparatus is contained within a tube 8 and since the barrier 3 is opaque optical coupling between the filament lamp 2 and the detector 4 is only achieved by light travelling into the timber 1 and along wood grain, the longitudinal axis of which is indicated by the arrow 9, to emerge from the wood and be received by the detector 4. The thickness of the barrier in the direction of the longitudinal axis of the grain is arranged to be approximately 2 mm. This distance was chosen because it has been found that the maximum contrast between light travelling from the source across the grain and light travelling source from a source along the grain is at a distance of 2 mm. from the centre of the source. The contrast at this distance is of the order of 50 : 1. Although the value of the threshold signal could be arranged to be variable and determined in dependence upon the average light received by the photodetector 4, since the contrast ratio of 50 : 1 is so large, it has been found that a simple fixed threshold level for the signal applied to the input terminal 6 is satisfactory.

It will be appreciated that in use of the apparatus, there will normally be coupling between the light source 2 and the detector 4 through the wood grain, but when a knot or blue staining or certain types of rot occur in the timber in a light path between the detector 4 and the filament lamp 2 coupling will be discontinued or at least reduced below the threshold level and indication of a defect is thereby facilitated. It may be arranged that the apparatus contained within the tube may be scanned across the wood for the detection of defects or alternatively it may be arranged that systems are provided whereby an image of the wood surface to be inspected is scanned across a light detector.

An array of detectors arranged side-by-side may be disposed in a line transverse to the longitudinal axis 9 of the wood grain for detection purposes. Alternatively an array of photodiodes may be provided across which is scanned an image of the wood to be inspected or on which is projected an image of the wood to be inspected and such an arrangement will be described with reference to FIG. 2a and FIG. 2b.

Referring now to FIG. 2a and FIG. 2b a photodiode array 10 has projected on to it a strip image as shown in FIG. 2b of a piece of timber 12 the image being reflected through a lens 13 by means of a mirror 14. The parts of the apparatus thus described are arranged on one side of an opaque barrier 15 the other side of which is a light source 16 arranged to project substantially parallel rays of light which are reflected by a mirror 17 to fall perpendicularly on to the surface of the timber 12. Since the lines or rays of light from the source 16 are substantially parallel they provide a well defined boundary 18 shown in FIG. 2b. The boundary is spaced apart by about 2mm. from the portion or strip 11 on the surface of the timber 12 which is projected on to the photodiode array 10 and which constitutes the image. The photodiodes of the array are scanned by conventional electronic scanning techniques. It will therefore be appreciated that as timber is moved past the apparatus, data may be fed from the photodiode array relating to the defects apparent in its surface.

Alternatively an arrangement may be provided as shown in FIGS. 3a and 3b wherein a helium neon (HeNe) laser 19 is used to produce a beam 20 which is directed on to the surface of a timber piece 21 to produce a spot 22. The grain direction of the timber piece is indicated by the arrow 23 and at a region spaced along the longitudinal axis of the grain, about 2mm. from the laser spot, an image represented by the spot 24 is reflected by means of mirrors 25 and 26 and reflected by a lens 27 on to a detector or detector array 28. Although not shown in FIG. 3a the detector may include an He Ne filter so as to be responsive only to laser light and to be substantially insensitive to non-coherent light produced for example by the floodlight 29 for a purpose to be explained later herein. The mirror 26 has a hole in it through which the laser beam 20 is directed to be reflected from the mirror 25 on to the timber piece 21. The mirror 25 is arranged to be rotatable or deflectable so that the spot 22 and the image 24 can be scanned across the timber sample 21. In accordance with the principles of the invention a defect will be indicated in dependence upon the intensity of the light reflected from the spot 24 defining the image.

Although the detector 28 of FIG. 3a may comprise a signal detector responsive to the intensity of the image 24 as compared with a fixed threshold level the detector 28 may alternatively comprise an arrangement as shown in FIG. 4. In this arrangement a detector system comprising detectors $D_1$, $D_2$, $D_3$, $D_4$ and $D_5$ which might be light sensitive diodes or transistors is provided. Detector $D_3$ is positioned so as to be coincident with the image of the spot and the detectors $D_1$ and $D_2$ are positioned orthogonally with respect to the detector $D_3$ so that detector $D_1$ receives reflected light which has travelled along the grain from the spot when the detector $D_2$ receives reflected light which has travelled across the grain from the spot or vice versa. The detectors $D_1$, $D_2$ and $D_3$ are each illuminated with reflected light which has been passed through an HeNe filter 30 which is tuned to the laser wavelength. Thus these detectors are substantially insensitive to ambient light and light from the floodlight 29. Light from the floodlight 29 is however reflected from a region 31 and passed via a half silvered mirror 32 to a red filter 33 and the detector $D_4$ on the one hand and via a blue filter 34 to detector $D_5$ on the other hand.

By comparing the outputs from detectors $D_1$ and $D_2$ a timber defect can be detected and by examining the colour of the defect i.e. blue or red which is indicated in dependence upon the relative amplitude of the outputs from detectors $D_4$ and $D_5$, the type of defect can be identified or at least classified to facilitate subsequent identification when mere data appertaining to the defect has been gathered by pattern recognition techniques for example in which the shape and configuration of the defect may be assessed.

One system for timber grading using the apparatus of FIG. 3 and FIG. 4 may be fabricated as shown in FIG. 5 wherein the detectors $D_1$, $D_2$ and $D_4$, $D_5$ are fed to comparators 35 and 36 respectively. The comparator 35 is arranged to provide an output signal when the output signal from the detector sensitive to light passing along the grain say $D_1$ is not substantially larger than the signal from the detector sensitive to light passing across the grain say $D_2$. Signals from the colour sensitive detectors $D_4$ and $D_5$ are compared in comparator 36 and if the blue signal is greater, blue stain or rot is indicated and signals from the comparator 35 are gated to line 37 whereas if the red signal is greater, signals from the comparator 35 are gated to line 38 indicating that the detected defect might most likely be a knot.

The signals are further processed in data processor 39 which might include a memory whereby the extent of a defect can be determined and consequently its shape and configuration. The foregoing data is assessed and the timber is graded accordingly.

The apparatus just before described is especially suitable for the detection of various types of knots it is also useful for detection of blue stain which is often described as yard blue or log blue etc. Blue stain is a fungus growth which affects the value of timber mainly because of the disfigurement it causes, and is a fungus growth which feeds upon the starchy contents of sapwood cells. It attacks the contents of the cells and replaces some of the cell contents with its own structure. Light incident upon the surface of wood which enters the cells is filtered by the cell walls the bulk of the light actually entering, propagating along and leaving the cells is contained in an infra-red band. The blue stain which permeates the cell attenuates very heavily light in this band. The attenuation is so great that transmission along a blue stain cell is smaller than propagation across normal cells. The same threshold value can therefore be utilised for the detection of blue stain.

By examining signals produced from the light detection devices in the arrangement described hereinbefore with reference to the accompanying drawings with character recognition apparatus of a comparatively simple kind it is possible to discriminate between knotwood and blue stain or other defects since each defect is characterised by its general shape and configuration. For example knotwood is usually in small well defined areas whereas blue stain occurs in streaks and larger irregular areas. It is therefore possible to discriminate fairly easily between knotwood and blue stain once both have been identified as defects.

In order to effect the recognition of these various defects, signals from light detectors are fed to the data processor and store which analyses the defects in the timber and provides a read-out corresponding to a particular grade appropriate to it.

Various modifications may be made to the apparatus just before described without departing from the scope of the invention and for example in the arrangement described with reference to FIGS. 3a and 3b the detector $D_3$ coincident with the laser spot which yields a direct image signal synchronised with the indirect image which may be useful for the isolation of certain knots and/or other defects.

A comprehensive system for timber grading may be provided by combining the apparatus of the present invention with apparatus as described in our British co-pending patent application No. 2473/74 entitled Improvements in or relating to timber inspection methods and apparatus, and No. 2474/74 entitled Improvements in or relating to methods and apparatus for profile monitoring.

What we claim is:

1. A method of detecting defects in sawn or planed timber comprising the steps of, directing a spot of light onto a surface of the timber, permitting said directed light to travel through the timber along an internal path from said spot to a region on the same surface of the timber in spaced-apart relationship with said spot, focussing the light emitted from said region onto light detector means, producing an electrical signal with said light detector means which reflects a defect in the timber and contemporaneously scanning said spot and said region from which light is focussed in said focussing step in a path across the timber so that timber defects in the path scanned are detected.

2. A method of grading lengths of sawn or planed timber having defects comprising the steps of directing a spot of light on to a surface of the timber, permitting said directed light to travel through the timber along an internal path from said spot to a region on the same surface of the timber in spaced-apart relationship with said spot, focussing the light emitted from said region onto light detector means, producing an electrical signal with said light detector means which reflects a defect in the timber and contemporaneously scanning said spot and said region from which light is focussed in said focussing so that timber defects in the path scanned are detected, and producing relative movement between the light detector means and the timber in a direction orthogonal to the direction of scanning so that the detection of defects along the length of the timber is facilitated and grading the timber length in accordance with the defects detected therein.

3. Apparatus for detecting defects in sawn or planed timber comprising, in combination, means for radiating light into timber to be inspected at a region of entry on the surface of the timber, light detector means for detecting light emerging from the timber on the same surface as the region of entry but at a location spaced-apart from the region of entry and for providing a first electrical signal which reflects a defect in the timber, means for providing a second electrical signal and comparator means for comparing the first electrical signal with the second electrical signal to produce an output signal related to the physical character of the timber.

4. Apparatus as claimed in claim 3 including an opaque barrier and wherein said light radiating means are disposed on one side of said barrier and wherein said light detector means are disposed on the other side of said barrier, a threshold detector operatively associated with said light detector means whereby an output signal from the threshold detector is produced when the signal from said light detector means bears a predetermined relationship to a preset threshold level signal constituting said second electrical signal.

5. Apparatus as claimed in claim 4, wherein said detector means comprises a plurality of photosensitive devices arranged in the form of an array and extending in side-by-side relationship across an inspection gate through which timber to be examined is passed.

6. Apparatus as claimed in claim 3 including means for directing a spot of light onto the surface of timber to be inspected, means for focussing light reflected from said location spaced-apart from said spot onto said light detector means and means for scanning said timber surface with said spot and for contemporaneously scanning the light detector means with light reflected from said location.

7. Apparatus as claimed in claim 6, comprising further light detector means onto which light from a further region of the timber under inspection is focussed, said further region being spaced substantially orthogonally from said location with respect to said spot, said further light detector means being arranged to provide said second electrical signal.

8. Apparatus as claimed in claim 7, wherein said means for directing said light spot comprises a laser, a filter arranged to pass light at the wavelength of the laser, said light detector means and said further light detector means being fed with light reflected from the timber via said filter.

9. Apparatus as claimed in claim 6, including two additional detectors for producing output signals, said additional detectors being responsive to red and blue light respectively reflected from the timber under inspection, further comparator means, gating means for producing output signals, said output signals from said additional detectors being compared in said further comparator means to produce output signals, means for feeding said output signals from said further comparator means to said gating means, means for feeding the output signals from said comparator means to said gating means whereby gating means output signals are indicative of the character of a detected timber defect.

10. Apparatus as claimed in claim 9, including data processing means having a memory whereby data appertaining to the presence of a defect and represented by signals from said comparator means, and data appertaining to the character of a detected defect and represented by signals from the said further comparator means are processed and utilized to provide an output signal indicative of the grade character or quality of the timber under inspection.

* * * * *